(12) United States Patent
Stothers et al.

(10) Patent No.: US 8,977,345 B2
(45) Date of Patent: Mar. 10, 2015

(54) MONITORING URODYNAMICS BY TRANS-VAGINAL NIRS

(76) Inventors: Lynn Stothers, Vancouver (CA); Andrew J. MacNab, Vancouver (CA); Babak Shadgan, Vancouver (CA)

( * ) Notice: Subject to any disclaimer, the term of this patent is extended or adjusted under 35 U.S.C. 154(b) by 1254 days.

(21) Appl. No.: 12/741,576

(22) PCT Filed: Nov. 5, 2008

(86) PCT No.: PCT/CA2008/001954
§ 371 (c)(1),
(2), (4) Date: May 12, 2011

(87) PCT Pub. No.: WO2009/059412
PCT Pub. Date: May 14, 2009

(65) Prior Publication Data
US 2011/0224553 A1    Sep. 15, 2011

Related U.S. Application Data

(60) Provisional application No. 60/996,167, filed on Nov. 5, 2007, provisional application No. 61/064,235, filed on Feb. 22, 2008.

(51) Int. Cl.
*A61B 5/00* (2006.01)
*A61B 5/20* (2006.01)

(52) U.S. Cl.
CPC ............... *A61B 5/202* (2013.01); *A61B 5/0075* (2013.01); *A61B 5/0084* (2013.01); *A61B 5/0086* (2013.01); *A61B 5/4519* (2013.01); *A61B 2503/40* (2013.01)
USPC .......................................... 600/473; 600/323

(58) Field of Classification Search
USPC ......... 600/310, 322, 323, 327, 328, 339–342, 600/407, 473, 475–479
See application file for complete search history.

(56) References Cited

U.S. PATENT DOCUMENTS

| | | | |
|---|---|---|---|
| 6,293,923 B1 * | 9/2001 | Yachia et al. | 604/96.01 |
| 6,836,688 B2 | 12/2004 | Ingle et al. | |
| 6,840,954 B2 | 1/2005 | Dietz et al. | |
| 2004/0236177 A1 | 11/2004 | Matlock | |
| 2005/0203419 A1 * | 9/2005 | Ramanujam et al. | 600/473 |
| 2006/0241530 A1 | 10/2006 | Ostrovsky et al. | |
| 2006/0276712 A1 | 12/2006 | Stothers et al. | |
| 2009/0270963 A1 * | 10/2009 | Pelger et al. | 607/138 |

OTHER PUBLICATIONS

English translation of the first Office Action dated Aug. 31, 2011, issued in the corresponding Chinese Patent Application No. 200880119781.9 (8 pages).

(Continued)

*Primary Examiner* — Ruth S Smith
(74) *Attorney, Agent, or Firm* — McDermott Will & Emery LLP

(57) ABSTRACT

The invention relate to the demonstration herein that it is feasible to use a transvaginal NIRS probe to interrogate functioning urological tissues, such as the urethral sphincter, the bladder detrusor muscle, and pelvic floor musculature, to obtain clinically relevant information. The present invention accordingly provides methods and devices for transvaginal monitoring or imaging of the urological tissues, such as the urethral sphincter and/or the bladder, and/or pelvic floor musculature, using NIRS.

21 Claims, 9 Drawing Sheets

(56) References Cited

OTHER PUBLICATIONS

Figure 1:
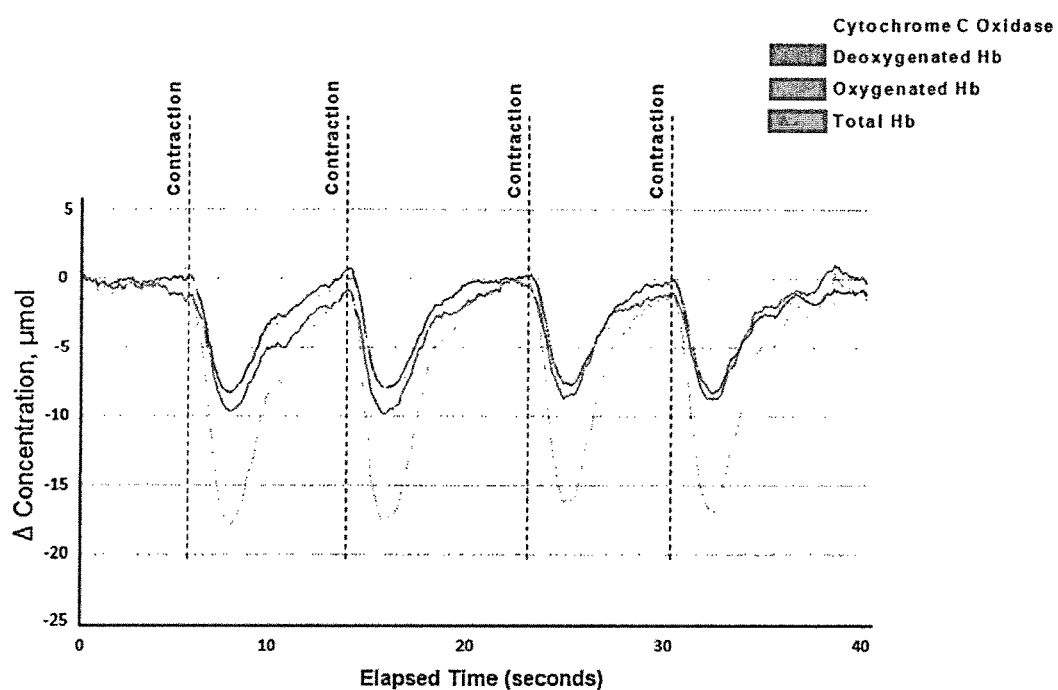

Aldrich, et al., "Fetal heart rate changes and cerebral oxygenation measured by near-infrared spectroscopy during the first stage of labour", European Journal of Obstetrics & Gynecology and Reproductive Biology (1996) pp. 189-195.

Van Beekvelt, et al., "Performance of near-infrared spectroscopy in measuring local O2 consumption and blood flow in skeletal muscle", Journal of Applied Physiology (2001) 90:511-519.

Rolfe, Peter, "In Vivo Near-Infrared Spectroscopy", Annu. Rev. Biomed. Eng. (2000) 02:715-754.

Wolf, et al., "Progress of near-infrared spectroscopy and topography for brain and muscle clinical applications", Journal of Biomedical Optics (2007) vol. 12(6) pp. 062104-1-062104-14.

Chance et al., "Recovery from exercise-induced desaturation in the quadriceps muscles of elite competitive rowers", Am J Physiol. (1992) 262(3 Pt 1):C766-75.

* cited by examiner

MONITORING URODYNAMICS BY TRANS-VAGINAL NIRS

FIELD OF THE INVENTION

The present invention relates to the field of physiological near-infrared spectroscopy (NIRS). The invention more specifically relates to the use of NIRS in diagnostic urological applications.

BACKGROUND

Urinary incontinence, or involuntary leakage of urine, is a condition which affects a significant portion of the population, but is especially prevalent in women (Melville et al. 2005). Urinary incontinence may present in different forms, such as stress incontinence and urge incontinence, or a mixture of forms. Continence relies on a number of factors, including relaxation of the detrusor muscles around the bladder wall, and proper activity of the urethral sphincter muscles and structures (including blood vessels) around the urethra (Smith et al. 2006). Abnormal muscle activity in the urinary bladder or urethral sphincter may also cause other problems, for instance overactive bladder or incomplete bladder emptying.

Abnormality of the detrusor muscles of the bladder, resulting in abnormal bladder function such as overactive bladder or urinary incontinence, may be caused by impairments, for instance, to the detrusor muscle activity or to the neurological connections to the detrusor muscle (Semins and Chancellor 2004). Monitoring of detrusor muscle activity provides useful information for a urologist in diagnosing or monitoring bladder function in patients with conditions such as urinary incontinence or overactive bladder. Conventional urodynamics procedures do not provide direct measurements of bladder muscle activity. Other imaging modalities have been utilized for this purpose, but also fail to provide detailed information on the activity of the detrusor muscle. For instance, ultrasonography has been used to determine bladder volume during bladder filling and voiding experiments in spinal cord injured animals (Keirstead et al. 2005). In another study, multi-slice echo-planar imaging was used to assess bladder volume and morphology.

Deficiency or abnormality of the urethral sphincter, resulting in urinary incontinence, can be caused by a number of different factors, for instance loss of urethral compression and support after pelvic surgery, childbirth, and pelvic trauma; lumbosacral neuropathy; and loss of muscle strength due to aging (Macura et al. 2006). Evaluation of the urinary sphincter muscles and other structures, such as blood vessels, may be achieved using a variety of known techniques, for instance urodynamics, cystourethroscopy, cystourethrography, ultrasonography and magnetic resonance imaging (Macura et al. 2006). There remains a need for improved devices and methods which allow accurate monitoring and/or imaging of the activity and status of urethral sphincter muscles and structures.

Urinary incontinence may often be associated with poor pelvic floor muscle strength and/or poor urinary sphincter muscle strength, which may or may not be a consequence of vaginal delivery during pregnancy. It is recognized that strengthening the pelvic floor muscles and/or urinary sphincter muscles may be beneficial, either during pregnancy to aid in delivery and prevent subsequent urinary incontinence issues, or in non-pregnancy related situations, for instance to improve or reduce urinary incontinence (Vasconcelos et al. 2006; de Oliveira et al. 2007). Using biofeedback during pelvic floor muscle or urinary sphincter muscle strengthening exercises is one method to improve the outcome of such exercises. Several methodologies are described in the literature to provide biofeedback monitoring during these kinds of exercises, which may include electromyography (EMG), perineometry, ultrasound, or measurement of intravaginal pressure (Peschers et al. 2001).

Near-infrared spectroscopy (NIRS) is a technique that has found use in a number of different biomedical applications, for instance monitoring of blood oxygenation and hemoglobin content, assessment of cerebral activity and evaluation of different tissues. In the near-infrared spectrum (particularly between 700 to 1100 nm), the primary absorbers of light in the context of the body are by chromophores in hemoglobin, oxyhemoglobin, water and lipids. In practice, NIR light penetrates tissues such as skin, bone, muscle and soft tissue where it is absorbed by the chromophores. These chromophores vary in their absorbance of NIRS light, depending on changes in oxygenation. Light in the visible spectrum (ie. 450-700 nm) penetrates tissue only short distances because it is usually attenuated by different tissue components. In the near-infrared spectrum, tissue penetration is much higher, up to several centimeters, allowing non-invasive monitoring of different tissue properties. For example, US Patent Publication 2006/0276712 discloses a method and devices for monitoring bladder detrusor muscle using near-infrared light through the skin.

The unique relation between the transparency of tissue to near infrared light and the specific absorption spectra of individual chromophores forms the basis of clinical near infrared spectroscopy. The principal chromophore of interest in studies using NIRS is hemoglobin which has a different extinction coefficient (absorption characteristic) across the NIR spectrum when oxygenated (O2Hb) and deoxygenated (HHb). Cytochrome-c-oxidase (CCO), the terminal enzyme of the mitochondrial respiratory chain, also absorbs light differently across the NIR spectrum depending on its redox status although the contribution of CCO to overall absorption is considerably less (approximately one tenth) than that of hemoglobin.

The majority of NIRS instruments used clinically are continuous wave units with lasers that transmit pulses of multiple wavelengths of light into the tissues, and sensors to detect the photons returning that are not absorbed. The changes in absorption at discrete wavelengths generate raw optical data that can be converted by software algorithms into concentration changes for each chromophore using a modification of the Lambert-Beer law. The related algorithms and software necessary for NIRS data to be used clinically also accommodate a number of limitations posed by the nature of human tissue, including the pathlength of NIR light and loss of photons undetected because of scattering beyond the field of view.

The full extent of the field through which light scatters is generally unknown in vivo, so that the initial concentration of each chromophore is generally unknown. Hence, clinical NIRS generally measures absolute changes in concentration relative to the initial baseline concentration. With real time sampling and graphic conversion of data, patterns of change in chromophore concentration and magnitudes of change are derived which can be used to infer physiologic change occurring within the tissue interrogated. Such changes include: an increase or decrease in O2Hb (an indirect measure of oxygen content); an increase or decrease in the total hemoglobin (change in blood volume); an abrupt decrease in O2Hb with simultaneous increase in HHb (ischemia); and a gradual decrease in O2Hb and increase in HHb (hypoxia). As cytochrome-c-oxidase drives>95% of O2 consumption and the synthesis of adenosine triphosphate (ATP) within mitochondria, changes in CCO redox status provide information relating to electron transport and oxidative phosphorylation at a cellular level. Interpretation of NIRS data that includes changes in O2Hb, HHb and CCO signals can offer important insights into oxygen utilization, energy dynamics and cellular well being.

Continuous wave NIRS instruments typically incorporate the following: a) at least one pulsed laser diode for each chromophore being sampled. Typically the lasers emit light in 1, 2 or 4 wavelengths in the 729 to 920 nm near infrared wavelength range with a 5 nm spectral width and pulse duration of 100 nanoseconds at 2 kHz cycle frequency; b) Fiberoptic bundles that transmit light from the source to a tissue interface (probe or patch) and back to the instrument; c) Optodes in the tissue interface that emit light into the tissue and receive the photons returning; d) Photon counting hardware (photomultiplier or photodiode); d) Computer with software containing algorithms for converting raw optical data into chromophore concentrations, storing and displaying data; e) A visual display where NIRS data are typically displayed graphically against time. Some instruments provide a choice from multiple wavelengths, and the option to use more than one data channel to allow comparison of different sites is available; a few incorporate additional spatial resolution that allows measurement of the ratio of oxygenated to total tissue hemoglobin which can be displayed as a measure of tissue oxygenation; and monitoring in the form of a regional map using arrays of emitters and receivers is possible.

SUMMARY OF THE INVENTION

Various aspects of the invention relate to the demonstration herein that it is feasible to use a transvaginal NIRS probe to interrogate functioning urological tissues, such as the urethral sphincter, the bladder detrusor muscle, and pelvic floor musculature, to obtain clinically relevant information. The present invention accordingly provides methods and devices for transvaginal monitoring or imaging of the urological tissues, such as the urethral sphincter and/or the bladder, and/or pelvic floor musculature, using NIRS.

In one aspect, the invention provides a near infrared spectrophotometric system adapted for transvaginal monitoring of a target tissue activity, for example non-invasive monitoring of a human patient for diagnostic purposes. The target tissue may for example be a urogenital muscle, or another tissue involved in urodynamics, such as a urethral sphincter, and/or a detrusor muscle of the bladder.

The system may include a probe body, which may for example be elongate and substantially tubular, having a generally smooth external surface, shaped for insertion into a vaginal lumen defined by vaginal walls. An external handle may be provided on the probe body, to facilitate positioning the probe so as to properly orient the optodes.

A near infrared light emitter may be housed in the probe body, for example in a position that permits near infrared light emitted by the emitter to pass out of the body, which may be by way of an emitter port portion of the body. A near infrared light collector may also be housed in the probe body, spaced apart from the emitter, in a position that permits near infrared light emitted by the emitter to traverse the vaginal walls, interact with a urogenital muscle, and pass back into the probe body, for example through a collector port portion of the body, before being collected by the collector as a collected light signal. The emitter and collector port portions of the body may for example be generally transparent to near infrared light, or may be adapted to include a light filter.

A near infrared light signal source may be provided, in communication with the emitter, to control the emission of near infrared light by the emitter. A near infrared light detector may also be provided, in communication with the collector, to detect the collected light signal. An external interface may be connected to the probe, for communicating with the light signal source and the light detector, for example to permit an operator to operate the light signal source and to monitor the collected light signal ex vivo.

In some embodiments, the near infrared light emitter and collector (optodes) may be separated by an interoptode distance in the probe that creates a path of photons that maximally interrogates the tissue of interest, rather than tissue superficial to or located deeper than the tissue of interest. The target tissue may accordingly be selected by a combination of probe positioning and interoptode distance, thereby avoiding non-target tissue such as the vaginal wall or tissue within the pelvis or the contents of the bladder. The probe and optode configuration may for example be selected to enable NIRS monitoring of changes in chromophore concentration in a) urogenital muscle in the pelvic floor, b) the detrusor muscle of the posterior wall of bladder, c) the urethral sphincter in the mid urethra and/or the sphincter's surrounding vascular plexus, and/or other tissue of physiologic interest anatomically related to the vagina.

An external interface may be provided that includes an output device, and the interface may be configured to display on the output device information that is indicative of an activity of the urogenital muscle.

In selected embodiments, a second infrared light collector is housed in the probe body, spaced apart from the emitter. The second collector may be positioned to permit near infrared light emitted by the emitter to traverse a second segment of the vaginal walls, interact with a second urogenital muscle, and pass back into the probe body, for example through a second collector port portion of the body, before being collected by the second collector.

In accordance with an alternative aspect of the invention, a method is provided for transvaginal NIRS monitoring of a target tissue, such as non-invasive monitoring of a human patient. To record periodic or continuous monitoring signals, the probe of the invention may be inserted into a vaginal lumen defined by vaginal walls. A near infrared light signal source may be operated, in communication with an emitter, to control the emission of near infrared light by the emitter, and a near infrared light detector, in communication with the collector, may be operated to monitor the collected light signal. An output device may be operated to display information that is indicative of an activity of the target tissue, such as a urogenital muscle.

In an alternative aspect, the invention provides an instrument for non-invasive transvaginal monitoring of a target tissue, such as urodynamic muscle activity. The instrument may include a probe body, as discussed above, with means provided for communicating with the probe body, comprising means for communicating a near infrared light signal to the emitter; and, means for communicating the collected light signal ex vivo. The means for communicating with the probe body may for example include a near infrared light signal source, in communication with the emitter to control the emission of near infrared light by the emitter; and, a near infrared light detector, in communication with the collector to detect the collection of near infrared light by the collector. The means for communicating with the probe body may further include an external interface communicating with the light signal source and the light detector, to permit an operator to operate the light signal source and to monitor the light detector ex vivo.

The invention further provides methods for transvaginal monitoring of a target tissue, such as non-invasive monitoring of a urodynamic muscle activity. The methods may involve positioning a near infrared light emitter within the vaginal lumen in proximity to the anterior vaginal roof, so that near infrared light emitted by the emitter traverses the vaginal roof and interacts with the target tissue, such as a urogenital muscle. A near infrared light collector may be positioned within the vaginal lumen in proximity to the anterior vaginal roof, spaced apart from the emitter, to collect light that has interacted with the urogenital muscle as a collected light signal. A near infrared light signal source in communication with the emitter may be operated so as to control the emission of near infrared light by the emitter. A near infrared light detector, in communication with the collector, may be operated so as to monitor the collected light signal, wherein the collected light signal provides information on the activity of the urodynamic muscle. The probe may for example be shaped so that the vaginal walls engage the probe to bias the emitter port and the collector port into juxtaposition with the anterior vaginal roof.

According to another aspect of the invention, there is provided a method for monitoring or imaging target tissues in a subject to provide biofeedback monitoring of tissues in a subject, the method comprising:
1) placing one or more NIRS emitters and/or one or more NIRS detectors into or onto a subject such that the NIRS emitter(s) and/or collector(s) are in close proximity to the target tissue;
2) emitting NIR light from the emitter(s) onto or through the target tissue while collecting NIR light that is reflected from or transmitted through the target tissue with the collectors(s);
3) detecting the collected the NIR light from the collector(s) using one or more light detector(s); and
4) sending the NIRS data to an output device which may be perceived in order to provide biofeedback monitoring.

According to some aspects of the invention the target tissue may be one or more of urinary sphincter, urinary bladder, or pelvic floor muscle tissue. According to another aspect of the invention, the NIR emitter(s) and/or collector(s) may be a component of an internal NIRS probe. According to another aspect of the invention, the NIR emitter(s) and/or collector(s) may be inserted into the body via the vagina and positioned in proximity to the target tissue. The emitter(s) and/or collector(s) may be a component of a vaginal NIRS probe. According to another aspect of the invention, the NIR emitter(s) and/or collector(s) may be inserted into the body via the urethra and positioned in proximity to the target tissue. The NIR emitter(s) and/or collector(s) may be a component of a urethral NIRS probe. According to another aspect of the invention, the NIRS emitter(s) and/or collector(s) may be inserted into the body via the rectum and positioned in proximity to the target tissue. The NIRS emitter(s) and/or collector(s) may be a component of a rectal NIRS probe. According to certain aspects of the invention, the biofeedback may be provided to aid with exercises designed to strengthen urinary sphincter muscles and/or pelvic floor muscles. The exercises may be Kegel exercises.

FIGURE DESCRIPTIONS

FIG. 1—illustrates biofeedback monitoring using data collected using an intravaginal NIRS probe of the invention, with fiberoptic emitter and receiver. The graph shows four NIRS tracings of urinary sphincter contractions (urethral sphincter).

Figure 2:
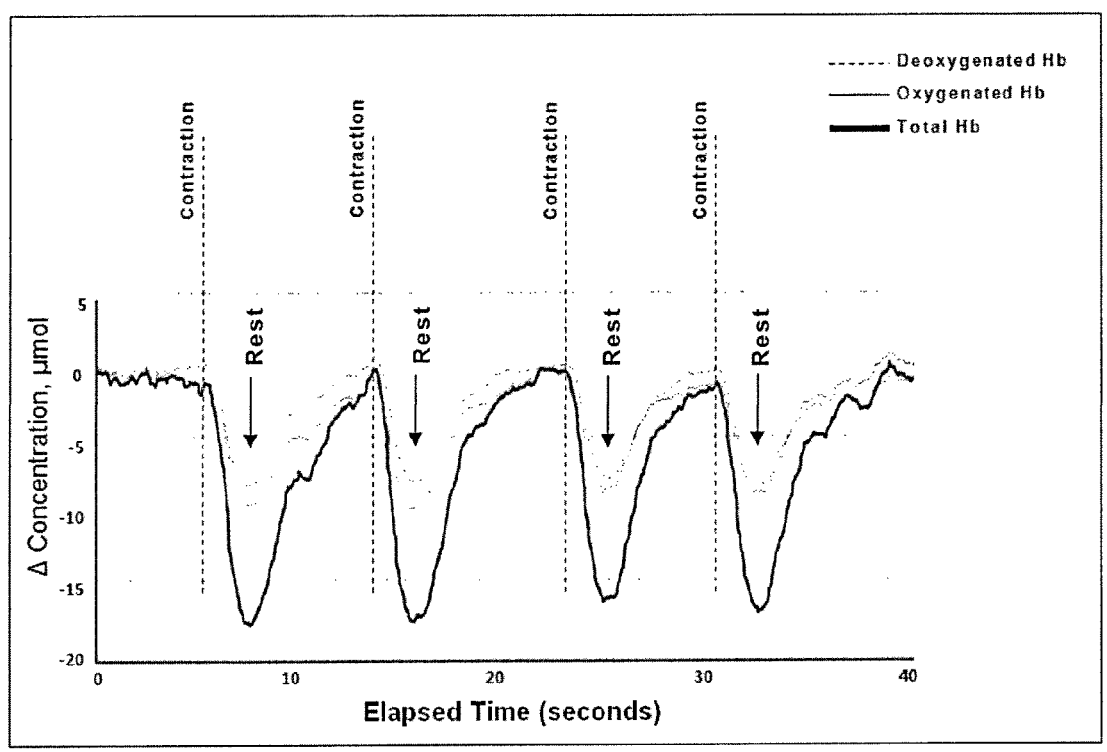

FIG. 2: illustrates NIRS data collected in accordance with the invention, showing a period of baseline, with stability of all 3 parameters followed by 4 repeated voluntary contractions of the pelvic floor held briefly and then released (showing the timing of each instruction to contract and to relax or rest).

Figure 3:
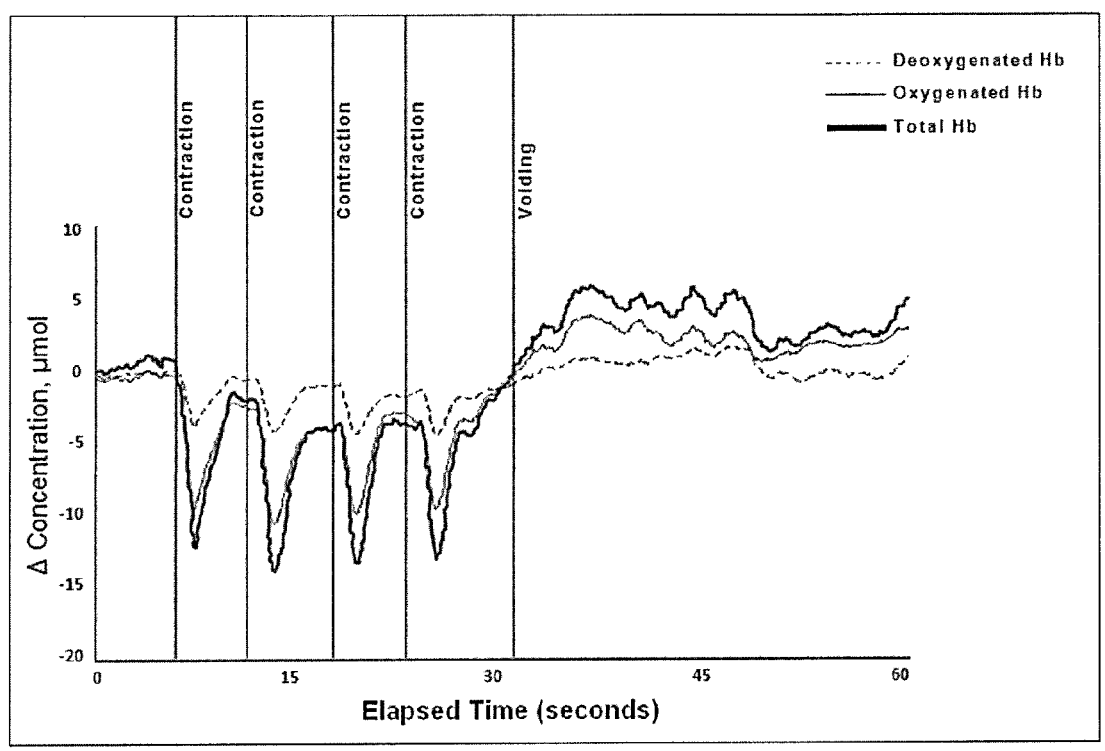

FIG. 3: Shows chromophore change on spontaneous voiding measured in the posterior wall of the detrusor (through the anterior vaginal wall), using a transvaginal NIRS monitoring system of the invention.

Figure 4:
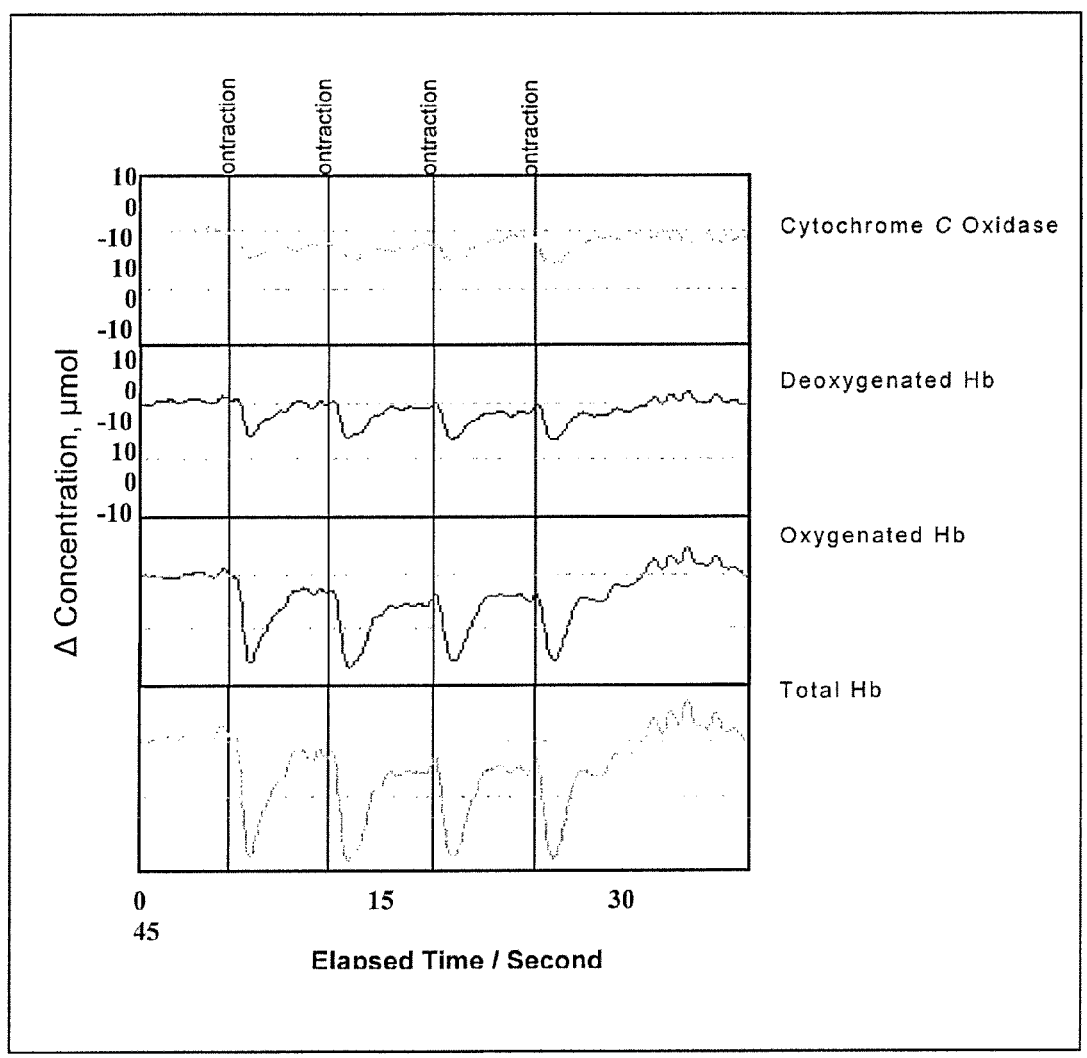

FIG. 4: Shows data for a period of baseline, with stability of 4 parameters, followed by 4 repeated voluntary contractions of the pelvic floor held briefly and then released, using a transvaginal NIRS monitoring system of the invention.

Figure 5:
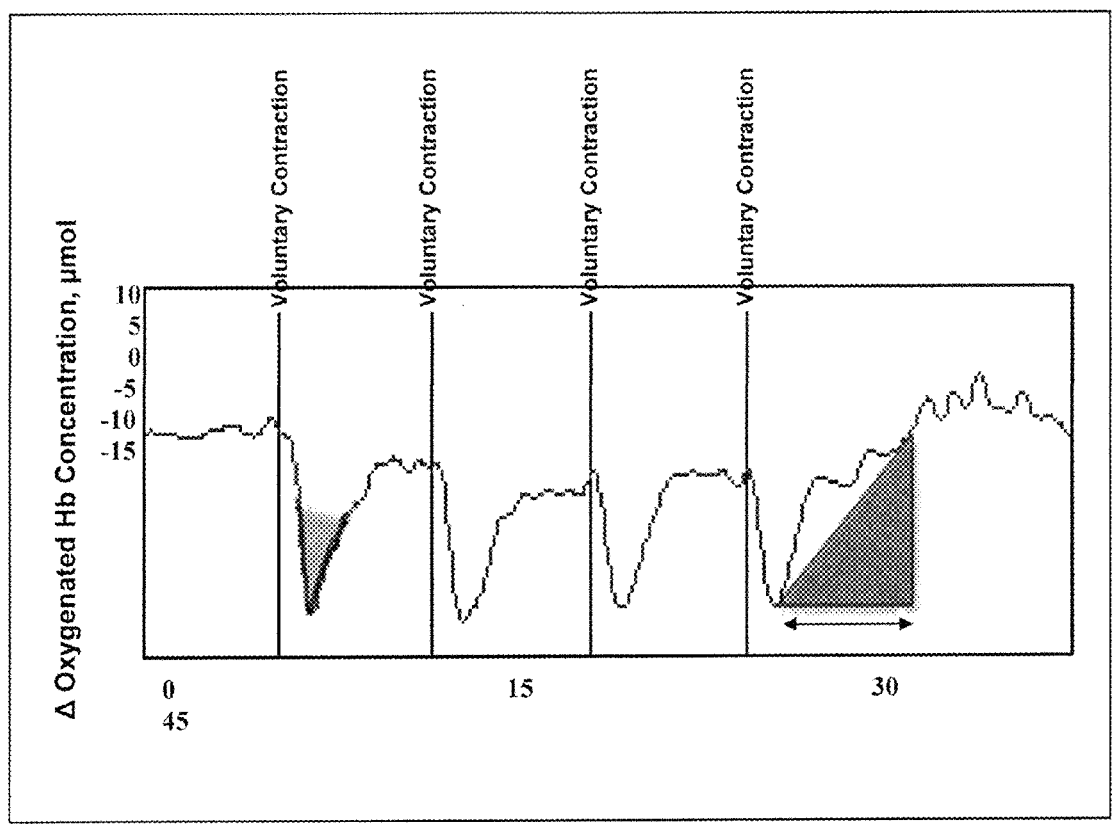

FIG. 5: Uses the oxygenated heamoglobin data from FIG. 4 to show that where NIRS parameters are measured during repetitive muscle contraction, the slope of the rate of change of HbO2 can be used to quantify the physiologic response/ reoxygenation of pelvic floor muscle. The HbO2 parameter is indicative of oxygen consumption, from which the 'fitness' or physiologic efficacy of the muscle can be quantified. The data captured by the vaginal probe in this Example is in accordance with the literature demonstrating that concentration changes of oxygenated hemoglobin of muscle measured by NIRS during exercise reflect the exercise intensity and the metabolic rate (Boushel et al., 1998).

Figure 6:
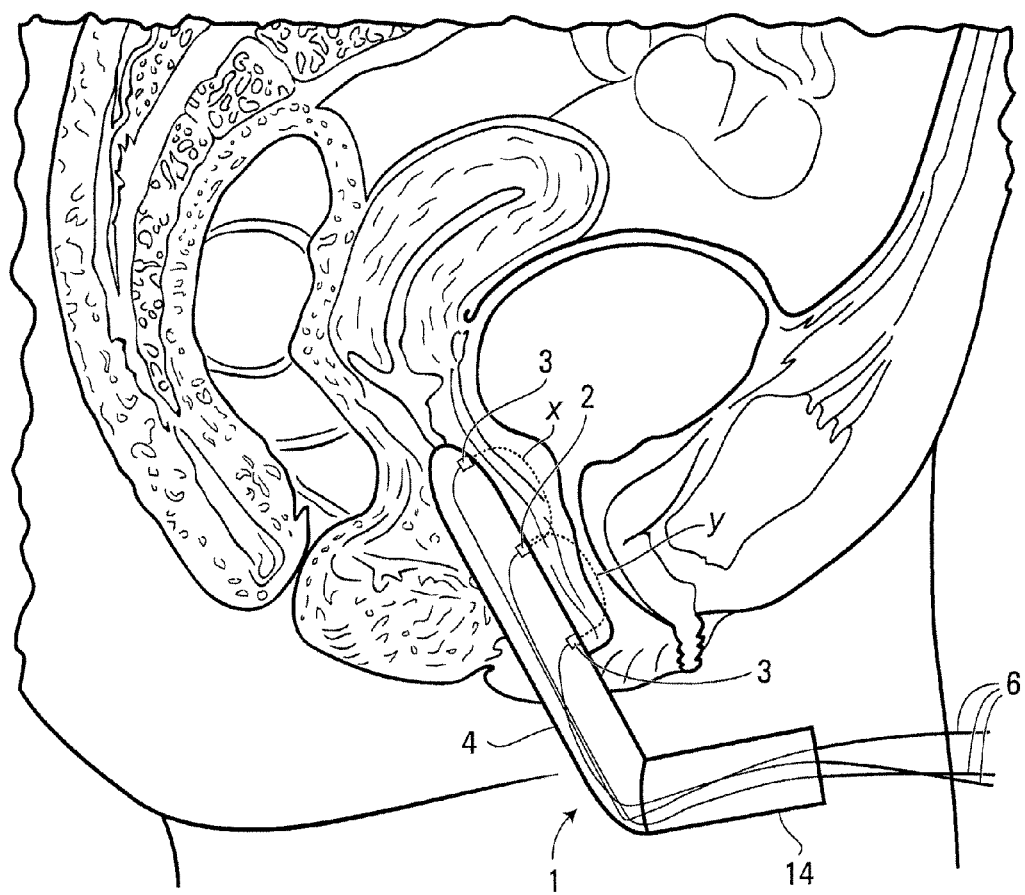
Figure 7:
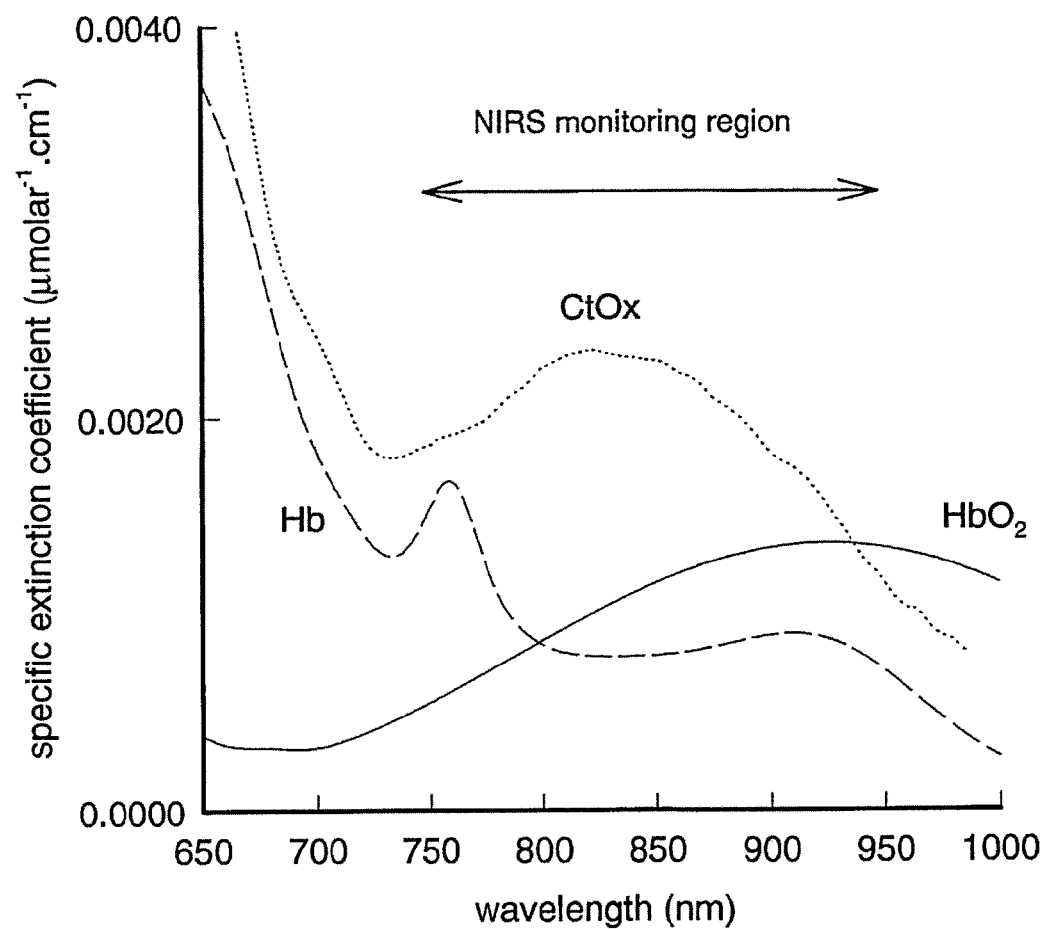

FIG. 6: Is a schematic illustration of the female genitourinary tract with placement of a NIRS probe of the invention within a vaginal lumen, illustrating a handle on the probe to assist in appropriate orientation and placement of optodes. This illustrated probe has an emitter and two sensors in the midline of the probe. As shown, the distal emitter sensor combination located towards the tip of the probe can be positioned anatomically and with an interoptode distance to allow NIRS monitoring of the posteror wall of the bladder detrusor muscle through the anterior wall of the vagina. The more proximal emitter sensor combination (closer to the handle of the probe) can be positioned anatomically and with the optimal interoptode separation FIG. 7: Is a graphic illustration of the extinction coefficients of adult Hb and the varying absorption of oxygenated hemoglobin (HbO2) deoxygenated hemoglobin (Hb) and cytochrome-c-oxidase (CtOx) across the NIR spectrum, reflecting the fact that alternative embodiments of the invention may use near infrared light of a variety of wavelengths, from about 700 nm to about 1300 nm (Delpy and Cope, 1997).

Figure 8:
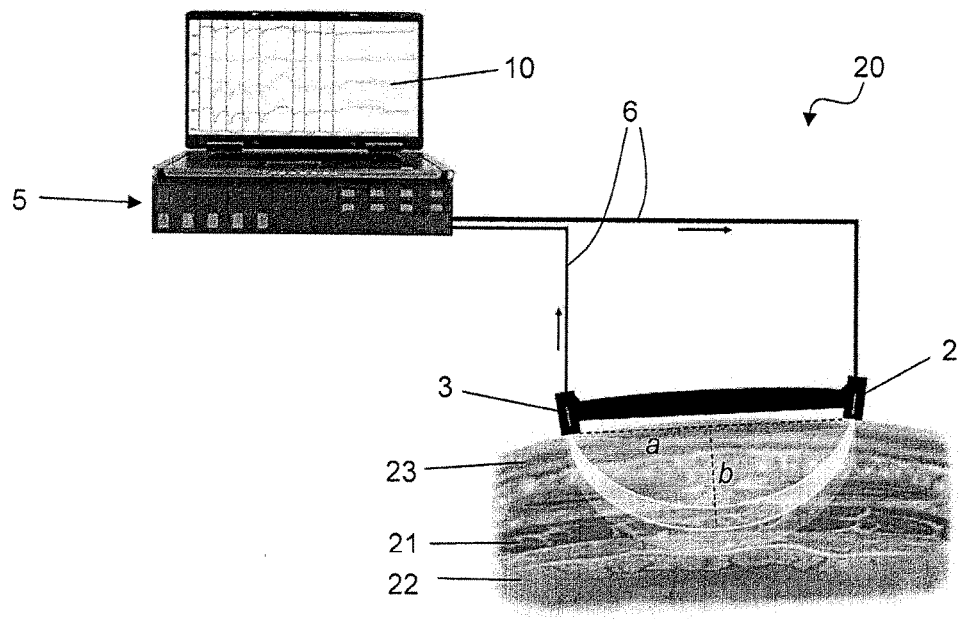

FIG. 8: is a schematic illustration of the configuration of a NIRS system of the invention for transvaginal interrogation of the bladder detrusor; illustrating the 'banana" shape of the photon path through tissue between the emitter and receiver of the optode (also illustrated schematically, in vivo in FIG. 6), and the effective depth of penetration for NIRS—approximately half the distance separating the emitter and receiver on the probe of the invention.

Figure 9:
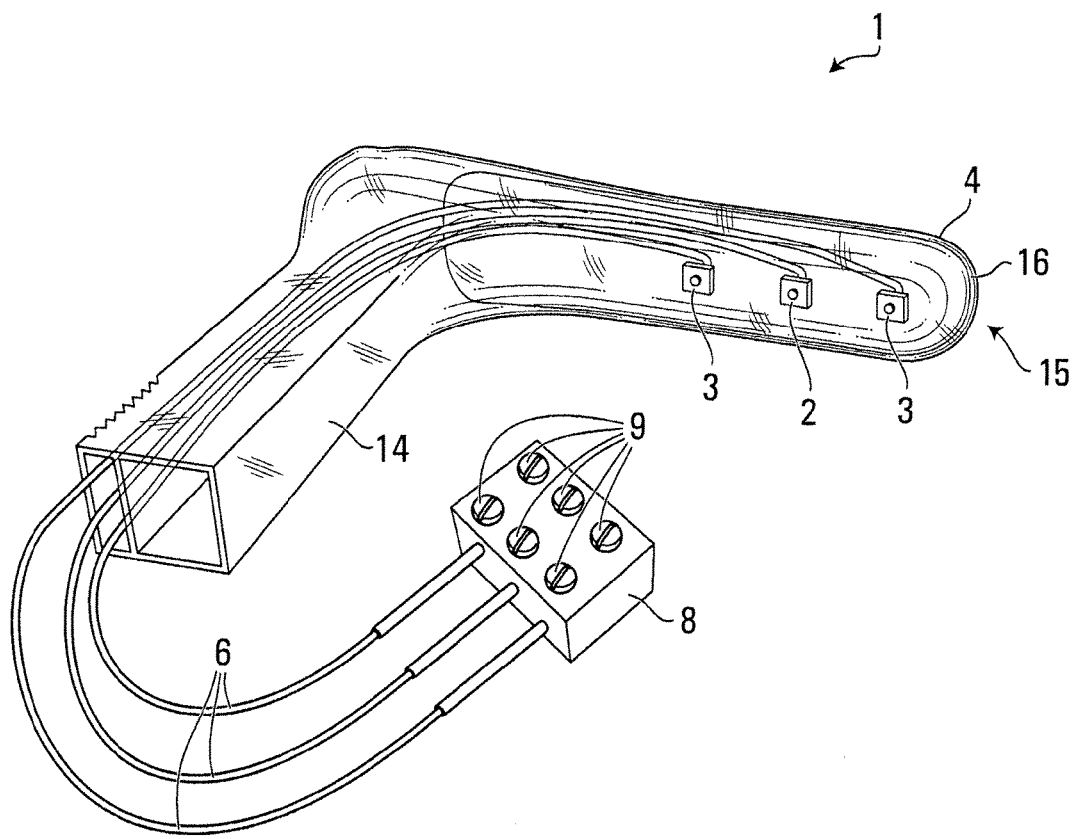

FIG. 9: Illustrates a probe of the invention, comprised of a body made of a disposable clear plastic vaginal speculum configured for bladder detrusor and mid-urethral monitoring. The emitter and sensors are shown (small silver squares) held in place by a foam insert. The proximal (sphincter) and distal (bladder) sensors and the emitter are attached to the three fine fibre-optic cables. These connect via an optical fibre interface (black block with retaining screws) to standard diameter cables from a NIRS instrument (not shown). The handle of the housing speculum facilitates correct positioning and stabilization during monitoring.

DETAILED DESCRIPTION

Definitions

As used herein a 'subject' refers to an animal, such as a bird or a mammal. Specific animals include rat, mouse, dog, cat, cow, sheep, horse, pig or primate. A subject may further be a human, alternatively referred to as a patient. A subject may further be a transgenic animal. A subject may further be a rodent, such as a mouse or a rat.

The term 'target tissue' refers to any tissue in a subject which may be analyzed using the methods and apparatus of the present invention. Such tissues may include, but not be limited to, tissues of the urological system, the reproductive system or the digestive system. Target tissues may also include tissues that surround or are connected to the tissues of the urological system, the reproductive system or the digestive system. According to some embodiments of the invention, the target tissues may be bladder tissue. According to some embodiments of the invention, the target tissues may be urethral sphincter tissue.

The 'urethral sphincter' may also be referred to as the 'sphincter urethrae'. The urethral sphincter is a collective name for the muscles used to control the flow of urine from the urinary bladder. These muscles surround the urethra, the tube which connects and allows flow of urine from the urinary bladder to the outside of the body. When the urethral sphincter muscles contract, the urethra is closed. There are two distinct areas of muscle: the internal sphincter, at the bladder neck and the external, or distal, sphincter. Human males typically have much stronger sphincter muscles than females.

The 'urinary bladder', also referred to herein as the 'bladder' is a hollow, muscular, and distensible (or elastic) organ that sits on the pelvic floor in mammals. It is the organ that collects urine excreted by the kidneys prior to disposal by urination. Urine enters the bladder via the ureters and exits via the urethra. The detrusor muscle is a layer of the urinary bladder wall made of smooth muscle fibers arranged in spiral, longitudinal, and circular bundles. When the bladder is stretched, this signals the parasympathetic nervous system to contract the detrusor muscle. This encourages the bladder to expel urine through the urethra. For the urine to exit the bladder, both the autonomically controlled internal sphincter and the voluntarily controlled external sphincter must be opened. Problems with these muscles can lead to incontinence.

The term 'pelvic floor muscle' refers to muscle fibers of the levator ani, the coccygeus, and associated connective tissue which span the area underneath the pelvis, it is important in providing support for pelvic viscera (organs), e.g. the bladder, intestines, the uterus (in females), and in maintenance of continence as part of the urinary and anal sphincters. Exercises which are designed to strengthen the pelvic floor muscles are often called 'Kegel exercises'.

'Near infrared' ('NIR') refers to any light within the range of 700 nm to 2500 nm. 'Near infrared spectroscopy' ('NIRS') refers to the analysis of NIR using spectrophotometric equipment. A 'NIRS device', alternately referred to herein as a 'NIRS instrument' or a 'NIRS system' typically comprises some or all of the following components: a NIR light source, a NIR light detector, a computer system to analyze the data or signal collected or produced by the detector and/or to control the light source, light guides to transmit light to and from the different components of the system and electrical connectors to transmit electrical signals to and from the different components of the system. A NIRS device may further comprise one or more of the following components: a light emitter and a light detector. An example of a NIRS device is the Oxymon MkIII continuous-wave near-infrared instrument available from Artinis Medical Systems (Netherlands). Other examples of NIRS instruments suitable to be used for the present invention would be known to one of skill in the art.

A 'light emitter', also referred to herein as an 'emitter', a 'NIR emitter', or a 'NIR light emitter' is any device suitable for directing or projecting NIR light onto, in or through the target tissue. A light emitter typically contains or is connected to a 'light source', also referred to herein as a 'NIR light source'. A light source is a device which is capable of generating NIR light, and may include, but not be limited to, a laser, laser lamp, LED or the like. Selection of an appropriate light source is well within the ordinary skill in the art in view of the present specification. In the context of the present invention, the light source may itself be the light emitter and thus provide NIR light directly to the target tissue. Alternately, the light source may be physically distinct from the light emitter, where the NIR light is actually provided to the target tissue. In this case, the light from the light source may be transmitted to the light emitter via a light guide, allowing the NIR light from the light source to travel through the light guide to the light emitter, where it is then directed or projected onto, in or through the target tissue. An example of a light guide suitable for the purposes of the invention is fiber optic cable. The light source may be controlled by external system software, which controls pulse timing of the power supply.

A 'light collector', also referred to herein as a 'collector' or a 'NIR light collector', is a device that is capable of receiving or collecting near-infrared light that is reflected from or transmitted through target tissue. The collected light may then be transmitted to another device for analysis, for instance a light detector. A 'light detector', also referred to herein as a 'detector' or a 'NIR light detector' is a device capable of separating the light reflected from or transmitted through the target tissue into wavelength regions of interest and providing a signal proportional to the emission of each of the regions of interest. Methods, apparatus and systems as described herein may comprise one, or more than one detector. In some embodiments of the invention, a light detector may itself function also as a light collector. In this fashion, the NIR light from the target tissue would be both collected and detected by the light detector. In other embodiments of the present invention, the light collector may be physically distinct from the light detector. In this case, the NIR light reflected from or transmitted through the target tissue that is collected by the light collector may be conducted from the light collector to the light detector by a light guide, thereby transmitting the collected light from the light collector to the light detector. A light detector may be controlled by system software, for example, and the start of acquisition and integration time may be synchronized with shuttering and pulsing of the light source and physiological events. Light detectors, as described as being part of the present invention, may be connected to, or may be an integral component of a NIRS instrument, as previously described.

In alternative aspects, the present invention provides methods and devices for monitoring of urological dynamics, including identifying, locating, monitoring, diagnosing and imaging of urological tissues such as the bladder and the urethral sphincter. In selected embodiments, it is feasible to obtain reproducible changes in chromophore concentration in the urethral sphincter, the posterior wall of the bladder detrusor and the pelvic floor. The application of the transvaginal systems of the invention to the bladder detrusor posterior wall is particularly clinically relevant, because in the obese patient, where suprapubic NIRS may not be possible, the vaginal approach offers an alternative means of obtaining detrusor data. In one aspect of the invention, physiologic change in the urethral sphincter and surrounding vascular plexus detected via NIRS adds additional physiologic information of relevance to the categorization of voiding dysfunction including urinary incontinence.

A subsidiary aspect of the invention is the recognition that there are branches of the voluntary urethral sphincter which are from the levator muscle, which contributes to both the urethral and anal sphincters. This is relevant because there are frequently coexisting degrees of relaxation particularly in women which involve the whole levator. The invention provides systems capable of interrogating these target tissues.

NIRS probes of the invention may incorporate other therapeutic or diagnostic components, such as components for alternative imaging protocols, such as ultrasound, MRI or Doppler, and or pressure probes which may for example contain EMG or electrical stimulation. In this way, NIRS data of the invention may be correlated with other diagnostic or treatment modalities. In some embodiments of the invention, the NIRS device may be used in conjunction with other medical devices, for instance an imaging device such as an ultrasound device, or a surgical device. In such a fashion, the NIRS probe system could be used to direct or guide the surgical devices, or could be used to monitor target tissues for other characteristics during the surgical procedure, thus allowing improved surgical treatment.

In one aspect, the invention provides a stand alone wireless unit. Patients may for example use such a system at home, for example to measure their consistency and compliance with pelvic floor exercises. Data may be collected in this way which would enable the efficacy of training on pelvic floor muscle to be quantified. In some embodiments of the invention, the NIRS device to be used for monitoring of target tissue may be portable. Various components of the device may be physically separate from other components of the device. A NIRS probe may for example contain NIR light emitter(s) and detector(s)/collector(s), and the output signal from the detector(s)/collector(s) may then be transmitted wirelessly to a remote location for further processing and subsequent display of the output signal. The output display may be a computer screen or a device monitor for visual output. Alternately, the output may be audio or tactile. The remote components of the device may communicate using various modes, which may include but is not limited to Bluetooth, Wi-Fi, optical, radio signal and the like.

In alternative embodiments, connections to the probe for signal communication may for example be by optical cables, which may for example communicate with a NIRS monitoring instrument, such as two channel NIRS monitor. Additional emitter sensor pairs may be added to the probe, and additional channels used on a multichannel instrument. Light emitting diodes (LEDs) may be used in the instrument in place of lasers and wireless technology employed, for example, to make a handheld wireless unit capable of transmitting data and graphics in realtime to a laptop or similar monitoring device. A spatially resolved configuration with a single emitter (LED or laser) and a series of sensors placed at fixed intervals from the emitter could also be used with the relevant software to optimally interrogate tissue at varying depths Systems of the invention have been used to obtain data in a series of studies, establishing that patterns of change in chromophore concentration detected by the systems of the invention are reproducible within patients during voluntary pelvic floor contraction. Patterns of change generated by coughing or voluntary valsalva maneuver, with increases in intra abdominal pressure, generate different patterns of change, with unique and reproducible features. During spontaneous voiding the patterns of change are comparable to those seen in the anterior wall of the detrusor when transcutaneous NIRS is performed.

One aspect of the invention relates to NIRS biofeedback monitoring of target tissues. Physiological changes in target tissues that are associated with urinary flow and function can be detected using a NIRS instrument, and that these changes can be utilized for biofeedback purposes. The inventors have further demonstrated that such physiological changes in the target tissues can be detected using NIRS across or through intervening tissue, such as the tissue between the vagina and urethra in a female subject.

With respect to the aspect of the invention relating to biofeedback, NIRS data of the invention can for example be used to quantify the efficacy of pelvic floor training exercises and provide a target for patients to optimize retraining. Pelvic floor NIRS data can also be analyzed using established methodologies, so that rates of change in oxyhemoglobin in particular provide information on rates of fatigue and hence improvements in muscle function resulting from biofeedback training techniques. Because of the high incidence of urinary incontinence secondary to pelvic floor dysfunction, a technique is needed to quantify the efficacy of biofeedback training.

In some embodiments, the invention provides methods for biofeedback monitoring of target tissues using a NIRS device. In certain embodiments of the invention, the NIRS device of the present invention may be utilized in a fashion such that the distal end of the probe device is in close proximity to the target tissues. In this way, the NIR light can be emitted by the light emitter onto the target tissue and the reflected or transmitted light can be collected and detected by the collector or detector, which is also in close proximity to the target tissue. The NIRS device may be a vaginal NIRS probe. In selected embodiments, the emitter(s) and/or collectors(s) of the internal NIRS device may be situated in close proximity to the target tissue, for instance urethral sphincter tissue. By utilizing a NIRS device as such, the output signal from the device may be presented to a subject for biofeedback monitoring purposes such that the subject may perceive the output signal and thus modulate their activity. The biofeedback may be used for pelvic floor muscle or urethral sphincter muscle strengthening activities. The strengthening activities may be Kegel exercises. The biofeedback may be used to monitor and evaluate therapeutic exercises. The biofeedback may be used to measure or quantify the effect of exercise on sphincter function or to define sphincter muscle fatigue, for instance during exercise. The output may be visual, audio, tactile or the like.

In various aspects of the invention, changes in NIRS chromophore concentration are evident during voiding that are different in health and disease. Data collected in accordance with the invention may for example be indicative of bladder pathologies that affect the physiology of the detrusor. For example, alterations in muscle thickness, contractility, oxygenation and hemodynamics may be observed. Data collected in accordance with the invention evidences a synchrony between the changes in chromophore concentration monitored via NIRS and the pressures measured via urodynamic testing during the bladder voiding cycle. This evidences an aspect of the invention, relating to monitoring of pressure derived effects on bladder function that can be detected via changes in oxygenation and hemodynamics.

Aspects of the invention involve the monitoring or diagnosis of a range of physiological characteristics, or pathologies. For example, properly characterizing the nature of a voiding dysfunction in females may involve both recording information from both the detrusor and sphincter muscles. Incontinence due to pelvic floor weakness would possibly need all three tissues evaluated. Biofeedback and pelvic floor training would mainly required pelvic floor muscle competence and recovery following voluntary contractions to be monitored but some sphincter info would likely be assessed at some stage too.

The configuration of the probe may be selected to make it possible to optimally monitor a tissue in locations where pathology is detectable. These locations may for example include the posterior wall of the bladder, the urethral sphincter and surrounding vascular plexus, and the muscles of the pelvic floor. Optimal monitoring requires that the NIRS emitter and sensor optodes are located in the anatomical proximity to the tissue of interest, with the separation between the optodes fixed so as to achieve optimal photon interrogation of the target tissue. FIG. 8 shows the configuration of a NIRS system (20) for interrogation of the bladder detrusor muscle (21) of bladder (22) through the vaginal wall (23). The interoptode distance (IOD) in effect focuses the NIRS interrogation so as to obtain the maximum amount of information from the target tissue. Interoptode distance may accordingly be optimized for alternative protocols, based on the principle that penetration of photons is optimal at a depth (FIG. 8, line b) below the optodes that is approximately half of the interoptode distance (FIG. 8, line a). In some embodiments, an approximate 2 cm interoptode distance may be selected to provide good penetration of photons to about 1 cm, for example to traverse the vaginal wall. A shorter IOD may be selected as a means for interrogation of more superficial layers, and a wider IOD selected for monitoring deeper tissues. Accordingly, the IOD is adjusted to provide optimal tissue penetration and monitoring of the selected target tissue. Ranges may for example be 1 to 3 cm. In an alternative approach, NIRS may be used in a spatially resolved configuration in which there is one emitter and there are several collectors, for example 3, with collectors at fixed distances from the emitter—for example 1, 1.5 and 2 cm. This configuration may be used to permit refined monitoring, providing collector signals that can be analyzed separately to provide information from alternative tissue depths.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

EXAMPLE

Biofeedback Monitoring of Urethral Sphincter via the Vagina using a NIRS Apparatus Urethral sphincter tissue was monitored in a female subject using an intravaginal NIRS apparatus. The apparatus (1) contained a NIRS emitter (2) and NIRS collectors (3) within a probe body (4) designed to be inserted into the female vagina (FIGS. 6 and 9). The NIRS emitter (2) and NIRS collectors (3) were connected to a NIRS spectroscope (5) via fiber optic cables (6) (FIG. 8). The NIRS spectroscope (5) used to control the NIRS emitter (2) and collectors (3) (FIG. 8) was the Artinis Medical Systems (Netherlands) Oxymon Mk III, which includes, a signal generator, a signal processor and a data analyzer. Four contractions of the urinary sphincter during urinary sphincter muscle exercises were detectable using this system (FIG. 1). The speed of recovery was observed to lengthen with each subsequent contraction, which may be a result of muscle fatigue.

The size of the emitter (2) and receiver (3) optodes was as follows: 3 mm wide, 8 mm long, and 4 mm deep, and the fine glass fiber cables (6) were small enough to incorporate into a probe body (4) having an external diameter of 2.0 mm (FIGS. 6 and 9). The 1.5 mm solid tip of each cable (6) was connected to the standard, larger diameter fibre-optic cables (not shown) of a commercial NIRS spectroscope (5) (FIG. 8), via a custom made interface (8) consisting of a plastic block with screw threaded holders (9) (FIG. 9). The Oxymon III generates NIR light in four wavelengths (764, 855, 904 and 975 nm) within an NIRS monitoring region (FIG. 7), incorporates a daylight filter to counter interference from ambient light, and has commercial software for conversion of raw optical densities into chromophore concentration and graphic display on a monitor (10) (FIG. 8).

Reproducible tracings were produced of changes in chromophore concentration ($O_2Hb$, $HHb$ and $tHb$) during spontaneous voiding (FIG. 3). Physiologic events repeated during each trial, such as voluntary coughing, Valsalva maneuver, and a series of voluntary pelvic floor contractions (FIGS. 1 to 5), each had a characteristic pattern of change. There was good reproducibility of the patterns and magnitude of change generated during sequential voluntary pelvic floor contractions in the channel monitoring over the mid-urethra, and an absence of significant movement artifact.

The paired NIRS collectors (3) were configured so that with the probe body (4) in position they would appose the bladder detrusor and mid-urethra respectively, through the anterior vaginal wall (FIGS. 6 and 9). The emitter (2) was placed mid-way between the collectors (3). Serial adjustments were made; the finalized distances selected were 1 and 5 cm from the tip (15) of the probe body (4) for the collectors (3) and 3 cm for the emitter (2) (FIG. 9). This provided good sampling sensitivity with an interoptode distance of 2 cm. The collectors (3) were laid on high density plastic foam (16) shaped to provide a snug push fit when inserted into the probe body (4) (FIG. 9). The dotted arcs x and y in FIG. 6 represent photon paths through tissue between the emitter (2) and the two collectors (3).

For monitoring, a urologist optimized the probe position, ensuring that it was in the midline, fully inserted, and oriented so as to direct the collectors (3) at the anterior roof of the vagina. Sensor orientation and correct insertion was aided by a visible vertical mark on the proximal end of the device (1). With the foam insert (16) cut to position the collectors (3) directly against the anterior wall of the housing, the optodes (2 and 3) are correctly aligned when the probe body (4) is inserted and the handle (14) held towards the patient in the midline.

The trans-vaginal NIRS data collected from the posterior wall of the detrusor muscle during bladder emptying was directly comparable to the patterns of chromophore change seen during transcutaneous monitoring of the anterior wall of the bladder detrusor via a suprapubic sensor in a large series of subjects. Also, the changes in NIRS parameters seen during pelvic floor contractions were particularly consistent by the standards of measurement of other studies of voluntary muscle contractions. There was also a clear difference between these patterns and those seen on voiding or individual events generated by cough or Valsalva. In addition, data collected over the detrusor and sphincter respectively were distinct, and were only detected in temporal relationship to voiding or individual events generated by voluntary physiologic activity.

REFERENCES

The following documents are incorporated herein by reference, with no admission that such documents constitute prior art with respect to the present invention, including priority U.S. Patent Application Nos. 60/996,167 and 61/064,235:

1. A. J. Wolfberg and A. J. du Plessis, Near-infrared spectroscopy in the fetus and neonate, Olin Perinatol. 33 (2006), 707-728.
2. Asgari S, Rohrborn H J, Engelhorn T, Stolke D. Intraoperative characterization of gliomas by near-infrared spectroscopy: possible association with prognosis. Acta Neurochir (Wien). 2003; 145(6):453-59.
3. Baena J R, Lendl B. Raman spectroscopy in chemical bioanalysis. Curr Opin Chem Biol 2004; 8:534-539.
4. Baert L, Berg R, Van Damme B, D'Hallewin M A, Johansson J, Svanberg K, Svanberg S. Clinical fluorescence diagnosis of human bladder carcinoma following low-dose Photofrin injection. Urology 1993; 41:322-30.
5. Bottiroli G, Croce A C. Autofluorescence spectroscopy of cells and tissues as a tool for biomedical diagnosis. Photochem Photobiol Sci 2004; 3:189-210.
6. Boushel R and Piantadosi C A. Near-infrared spectroscopy for monitoring muscle oxygenation. Acta Physiol Scand 2000; 168:615-22.
7. Boushel R, Lang berg H, Olesen J, Gonzales-Alonzo J, Bulow J and Kjaer M, Monitoring tissue oxygen availability with near infrared spectroscopy (NIRS) in health and disease. Scand J Med Sci Sports 2001; 11:213-22.
8. Boushel R. Pott F. Madsen P. Radegran G. Nowak M. Quistorff B. Secher N. Muscle metabolism from near infrared spectroscopy during rhythmic handgrip in humans. European Journal of Applied Physiology & Occupational Physiology. 79(1):41-8, 1998 December.
9. Brazy J E, Lewis D V, Mitnisk M H, and Jobsis-VanderVliet F F, Noninvasive monitoring of cerebral oxygenation in preterm infants: preliminary observation. Pediatrics 1985; 75:217-25.
10. Burnett A L, Allen R P, Wright D C, Davis, Wright D C, Trueheart I N, Chance B. Near infrared spectrophotometry for the diagnosis of vasculogenic erectile dysfunction. Int J Impot Res 2000; 12:247-54.
11. C. J. Aldrich, D. D'Antona, J. A. Spencer, D. T. Delpy, E. O. R. Reynolds and J. S. Wyatt, Fetal heart rate changes and cerebral oxygenation measured by near-infrared spectroscopy during the first stage of labour, Eur J Obs Gynecol and Rep Biol. 64 (1996), 189-195.
12. C. J. Aldrich, D. D'Antona, J. A. Spencer, J. S. Wyatt, D. M. Peebles, D. T. Delpy and E. O. R. Reynolds, Late fetal heart rate decelerations and changes in cerebral oxygenation during the first stage of labour, Br J Obstet Gynaecol. 102(1) (1995), 9-13.
13. C. J. Aldrich, D. D'Antona, J. S. Wyatt, J. A. Spencer, D. M. Peebles and E. O. R. Reynolds, Fetal cerebral oxygenation measured by near-infrared spectroscopy shortly before birth and acid-base status at birth, Obstet Gynaecol. 84 (1994), 861-866.
14. Capraro G A, Mader T J, Coughlin B F, Lovewell C, St Louis M R, Tirabassi M, Wadie G, Smithline H A. Feasibility of using near-infrared spectroscopy to diagnose testicular torsion: an experimental study in sheep. Ann Emerg Med 2007; 49:520-5.
15. Colier W N, Froeling F M, de Vries J D, Oesburg B. Measurement of the blood supply to the abdominal testis by means of near infrared spectroscopy. Eur Urol 1995; 27:160-6.
16. Crow P, Barrass B, Kendall C, Hart-Prieto M, Wright M, Persad R, Stone N. The use of Raman spectroscopy to differentiate between different prostatic adenocarcinoma cell lines. Br J Cancer 2005; 92:2166-70.
17. Crow P, Molckovsky A, Stone N, Uff J, Wilson B, Wong KeeSong L M. Assessment of fiberoptic near-infrared raman spectroscopy for diagnosis of bladder and prostate cancer. Urology 2005; 65:1126-30.
18. Crow P, Stone N, Kendall C A, Persad R A, Wright M P. Optical diagnostics in urology: current applications and future prospects. BJU Int 2003; 92:400-7.
19. Crow P, Stone N, Kendall C A, Uff J S, Farmer J A, Barr H, Wright M P. The use of Raman spectroscopy to identify and grade prostatic adenocarcinoma in vitro. Br J Cancer 2003; 89:106-8.
20. D. Piao, H. Xie, W. Zhang and J. S. Kraminski, Endoscopic, rapid near-infrared optical tomography, Opt Lett. 31(19) (2006), 2876-78.
21. D. M. Peebles, A. D. Edwards, J. S. Wyatt, A. P. Bishop, M. Cope, D. T. Delpy and E. O. R. Reynolds, Changes in human fetal cerebral hemoglobin concentration and oxygenation during labor measured by near-infrared spectroscopy, Am J Obstet Gynecol. 166(5) (1992), 1369-1373.
22. D. M. Peebles, Cerebral hemodynamics and oxygenation in the fetus: The role of intrapartum near-infrared spectroscopy, Neurologic Disorders in the Newborn. 24(3) (1997), 547-565.
23. D. N. Harris, F. M. Cowans, D. A. Wertheim and S. Hamid, NIRS in adults—effects of increasing optode separation, Adv Exp Med Biol. 354 (1994), 837-841.
24. De Blasi R A, Ferrari M, Natali A, Conti G, Mega A, Gasparetto A. Noninvasive measurement of forearm blood flow and oxygen consumption by near-infrared spectroscopy. J Appl Physiol 1994; 76(3): 1388-93.
25. de Oliveira, C., M. A. Lopes, et al. (2007). "Effects of pelvic floor muscle training during pregnancy." Clinics 62(4): 439-46.
26. Delpy D T, Cope M, Zee P van der, Arridge S, Wray S, Wyatt J. Estimation of optical pathlength through tissue from direct time of flight measurements. Phys med Biol. 1988; 33: 1433-1442.

27. Delpy D T, Cope M., Quantification in tissue near-infrared spectroscopy. Phil Trans R Soc Lond B 1997; 352:649-659.
28. Diesel W, Noakes T D, Swanepoel C, Lambert M. Isokinetic muscle strength predicts maximum exercise tolerance in renal patients on chronic hemodialysis. Am J Kidney Dis 1990; 16:109-114.
29. Evan A P, Coe F L, Lingeman J E, Shao Y, Matlaga B R, Kim S C, Bledsoe S B, Sommer A J, Grynpas M, Phillips C L, Worcester E M. Renal crystal deposits and histopathology in patients with cystine stones. Kidney Int; 2006; 69:2227-35.
30. Ferrari M, Binzoni T, Quaresima V. Oxidative metabolism in muscle. Philos Trans R Soc Lond B Biol Sci 1997; 352(1354): 677-83.
31. Ferrari M, Mottola L, Quaresima V. Principles, techniques and limitations of near infrared spectroscopy. Can J Appl Physiol 2004; 29:463-487.
32. G. Rau, E. Schulte, C. Disselhorst-Klug, From cell to movement: to what answers does EMG really contribute?, J Electromyogr Kines, 14(5) (2004), 611-7.
33. Gagnon R. Macnab A J, Gagnon F. Brain, spine and muscle Cu-A redox patterns of change during hypothermic circulatory arrest in swine. Comp Biochem Phys A 2005; 141(3):264-70.
34. Gagnon R E, Macnab A J, Near Infrared spectroscopy (NIRS) in the clinical setting—An adjunct to monitoring during diagnosis and treatment. Spectroscopy 2005; 19:221-233.
35. Hamaoka T. McCully K. K. Quaresima V, Yamamoto K and Chance B. Near-infrared spectroscopy/imaging for monitoring muscle oxygenation and oxidative metabolism in healthy and diseased humans. J Biomed Optics 2007; 12(6):0621051-12.
36. Homma S, Eda H. Ogasawara S. Kagaya A. Near-infrared estimation of O2 supply and consumption in forearm muscles working at varying intensity. J Appl Physiol 1996; 80 (4) 1279-1284.
37. Hong T D, Phat O. Plaza P. Daudon M, Dao N Q. Identification of urinary calculi by Raman laser fiber optics spectroscopy. Clin Chem 1992; 38:292-8.
38. Hostetter T H, Wilkes B M, Brenner B M, 1980. Mechanisms of impaired glomerular filtration in acute renal failure. In: Brenner B M, Stein J H, eds. Contemporary issues in nephrology. 6th Ed. New York, N.Y.: Churchill-Livingstone; 1980:52-78.
39. Jarvis R M, Goodacre R. Ultra-violet resonance Raman spectroscopy for the rapid discrimination of urinary tract infection bacteria. FEMS Microbiol Letters 2004; 232: 127-32.
40. Jobsis F F, Noninvasive, infrared monitoring of cerebral and myocardial oxygen sufficiency and circulatory parameters, Science 1977; 198:1264-7.
41. Jones R N. Analytical applications of vibrational spectroscopy, a historical review, in; Chemical. Biological, and Industrial Applications of Infrared Spectroscopy. John Wiley and Sons, New York, 1985, pp. 1-43.
42. Katzberg R W. Urography in the 21st century: New contrast media, renal handling, imaging characteristics, and nephrotoxicity. Radiology 1997; 204:297-312.
43. Keirstead, H. S., V. Fedulov, et al. (2005). "A noninvasive ultrasonographic method to evaluate bladder function recovery in spinal cord injured rats." Exp Neurol 194(1): 120-7.
44. Kemp G J, Crowe A V, Anijeet H K, Gong Q Y, Bimson W E, Frostick S P, Bone J M, Bell G M, Roberts J N. Abnormal mitochondrial function and muscle wasting, but normal contractile efficiency, in haemodialysed patients studied non-invasively in vivo. Nephrol Dialys Transplan 2004; 19:1520-7.
45. Koenig F, McGovern F J, Enquist H, Larne R, Deutsch T F, Schomacker K T. Autofluorescence guided biopsy for the early diagnosis of bladder carcinoma. J Urol 1998; 159:1871-5.
46. Kondo, Y., Y. Homma, et al. (2001). "Transvaginal ultrasound of urethral sphincter at the mid urethra in continent and incontinent women." J Urol 165(1): 149-52.
47. Krause W, Muschick P, Kruger U. Use of near-infrared reflection spectroscopy to study the effects of X-ray contrast media on renal tolerance in rats: effects of a prostacyclin analogue and of phosphodiesterase inhibitors. Invest Radiol 2002; 37:698-705.
48. Latimer P. Absolute adsorption and scattering spectrophotometry. Arch Biochem Bio 1967; 119:580-581.
49. Lin D L, Tarnowski C P, Zhang J, Dai J, Rohn E, Patel A H, Morris M D, Keller E T. Bone metastatic LNCaP-derivative C4-2B prostate cancer cell line mineralizes in vitro. Prostate 2001; 47:212-21.
50. Liss P, Nygren A, Olsson U, Ulfendahl H R, Erikson U. Effects of contrast media and mannitol on renal medullary blood flow and red cell aggregation in the rat kidney. Kidney Int 1996; 49:1268-1273.
51. Lorincz A, Haddad D, Naik R, Naik V, Fung A, Cao A, Manda P, Pandya A, Auner G, Rabah R, Langenburg S E, Klein M D. Raman spectroscopy for neoplastic tissue differentiation; a pilot study. J Ped Surg 2004; 39:953-6.
52. Low J A, Froese A B, Galbraith R S, Smith J T, Sauerbrei E E, Derrick E J. The association between preterm newborn hypotension and hypoxemia and outcome during the first year. Acta Paediatr 1993; 82: 433-437.
53. M. Doyle, P. M. S. O'Brien, Y. A. Wickramsinghe. R. J. F. Houston and P. Rolfe, Near infrared spectroscopy used to observe changes in fetal cerebral haemodynamics during labour, J Perinatol. 22(3) (1994), 265-268.
54. M. Wolf, G. Duc, M. Keel, P. Niederer, K. von Siebenthal, and H. U. Bucher, Continuous noninvasive measurement of cerebral arterial and venous oxygen saturation at the bedside in mechanically ventilated neonates. Crit. Care Med. 1997; 25(9):1579-1582.
55. M. C. P. van Beekvelt, B. G. M. van Engelen, R. A. Wevers and W. J. M. Colier, In vivo quantitative near-infrared spectroscopy in skeletal muscle during incremental isometric handgrip exercise, Clin Physiol & Fun Im. 22 (2002), 1-8.
56. M. C. P. van Beekvelt, M. S. Borghuis, B. G. M. van Engelen, R. A. Wevers and W. N. Colier, Adipose tissue thickness affects in vivo quantitative near-IR spectroscopy in human skeletal muscle, Clin Sci. (London) 101(1) (2001), 21-28.
57. Macnab A J, Gagnon R E, Gagnon F A, LeBlanc J G. NIRS monitoring of brain and spinal cord—detection of adverse intraoperative events. Spectroscopy 2003; 17:483-490.
58. Macnab A J, Gagnon R E, Stothers L. Clinical NIRS of the urinary bladder—A demonstration case report, Spectroscopy 2005; 19:207-212.
59. Macura, K. J., R. R. Genadry, et al. (2006). "MR imaging of the female urethra and supporting ligaments in assessment of urinary incontinence: spectrum of abnormalities." Radiographics 26(4): 1135-49.
60. Matsumoto N, Ichimura S, Hamaoka T, Osada T, Hattori M, Miyakawa S. Impaired muscle oxygen metabolism in uremic children: improved after renal transplantation. Am J Kidney Dis 2006; 48:473-80.

61. Melville, J. L., W. Katon, et al. (2005). "Urinary incontinence in US women: a population-based study." Arch Intern Med 165(5): 537-42.
62. Meuleman E J, Diemont W L. Investigation of erectile dysfunction: diagnostic testing for vascular factors in erectile dysfunction. Ural Olin N Amer 1995; 22: 803.
63. Mitsuta H, Ohdan H. Fudaba Y, Irei T, Tashiro H, Itamoto T, Asahara T. Near-infrared spectroscopic analysis of hemodynamics and mitochondrial redox in right lobe grafts in living-donor liver transplantation. Am J Transplant. 2006; 6(4):797-805.
64. Neary J P. Application of near infrared spectroscopy to exercise sports science. Can J Appl Physiol 2004; 29:488-503.
65. Obrig H, Villringer A. Beyond the visible—imaging the human brain with light. J Cereb Blood Flow Metab. 2003; 23(1):1-18.
66. P. Rolfe, In vivo near-infrared spectroscopy, An Rev Biomed Eng. 2 (2000), 715-754.
67. Peschers, U. M., A. Gingelmaier, et al. (2001). "Evaluation of pelvic floor muscle strength using four different techniques." Int Urogynecol J Pelvic Floor Dysfunct 12(1): 27-30.
68. Petrova A, Mehta R. Near-infrared spectroscopy in the detection of regional tissue oxygenation during hypoxic events in preterm infants undergoing critical care. Ped Crit Care Med 2006; 7:449-54.
69. Quaresima V, Springett R, Cope M, Wyatt J T, Delpy D T, Ferrari M, Cooper C E. Oxidation and reduction of cytochrome oxidase in the neonatal brain observed by in vivo near infrared spectroscopy. Biochim Biophys Acta 1998; 1366(3):291-300.
70. Rodriguez-Segade S, Alonso de la Pena C, Paz J M, Novoa D, Arcocha V, Romero R, Del Rio R. Carnitine deficiency in haemodialysed patients. Olin Chim Acta 1986; 159:249-256.
71. S. Schmidt, A. Lenz, H. Eilers, N. Helledie and D. Krebs, Laser spectrophotometry in the fetus, J Perinat Med. 17(1) (1989), 57-62.
72. S. Schmidt, S. Gorinssen, H. Eilers, H Fahnenstich, A. Darer and D. Krebs, Animal experiments for the evaluation of laser spectroscopy in the fetus during labor, J Perinat Med. 19(1-2) (1991), 107-13.
73. Semins, M. J. and M. B. Chancellor (2004). "Diagnosis and management of patients with overactive bladder syndrome and abnormal detrusor activity." Nat Clin Pract Urol 1(2): 78-84; quiz 109.
74. Shadgan B, Stothers L, Macnab A J. A transvaginal probe for near infrared spectroscopic monitoring of the bladder detrusor muscle and urethral sphincter. Spectroscopy. In Press
75. Smith, P. P., R. J. McCrery, et al. (2006). "Current trends in the evaluation and management of female urinary incontinence." Cmaj 175(10): 1233-40.
76. Spargias K, Adreanides E, Giamouzis G, Karagiannis S, Gouziouta A, Manginas A, Voudris V, Pavlides G, Cokkinos DV. Iloprost for prevention of contrast-mediated nephropathy in high-risk patients undergoing a coronary procedure. Results of a randomized pilot study. Eur J Clin Pharm 2006; 62:589-95.
77. Stone N, Kendall C, Smith J, Crow P, Barr H. Raman spectroscopy for identification of epithelial cancers. Faraday Disc 2004; 126:141-57.
78. Stothers L, Macnab A, Gagnon R. A description of detrusor cellular respiration during urodynamics in humans using non invasive near infrared spectroscopy. J Urol (Suppl) 2006; 175(4):446.
79. Stothers L, Macnab A, Gagnon R. Changes in cytochrome C levels in the human bladder during the filling and emptying cycle. J Urol (Suppl) 2005; 173(4): 353-354.
80. Stothers L, Macnab A, Gagnon R. Non invasive urodynamics using near infrared spectroscopy in the human. J Urol (Suppl) 2005; 173(4): 354.
81. Stothers L, Macnab A, Gagnon R. Patterns in detrusor oxygenation during flow and pressure flow studies in men using near infrared spectroscopy (NIRS). J Urol (Suppl) 2006; 175(4):444.
82. Stothers L, Macnab A. Near-infrared Spectroscopy (NIRS) changes in oxy and deoxyhemoglobin during natural bladder filling and voiding in normal volunteers. J Urol (Suppl) 2007; 177(4):506.
83. Svensson T, Andersson-Engels S, Einarsdottir M, Svanberg K. In vivo optical characterization of human prostate tissue using near-infrared time-resolved spectroscopy. J Biomed Optics. 2007; 1291:014022.
84. Tachtsidis I, Tisdall M, Leung T S, Cooper C E, Delpy D T, Smith M, Elwell C E. Investigation of in vivo measurement of cerebral cytochrome-c-oxidase redox changes using near-infrared spectroscopy in patients with orthostatic hypotension. Physiol Meas. 2007; 28:199-211.
85. Takasaki E. Carbonate in struvite stone detected in Raman spectra compared with infrared spectra and X-ray diffraction. Intl J Urol 1996; 3:27-30.
86. Tauber S, Stepp H, Meier R, Bone A, Hofstetter A, Stief C. Integral spectrophotometric analysis of 5-aminolaevulinic acid-induced fluorescence cytology of the urinary bladder. BJU Int 2006; 97:992-6.
87. Tortoriello T A, Stayer S A, Mott A R, McKenzie E D, Fraser C D, Andropoulos D B, Chang A C. A noninvasive estimation of mixed venous oxygen saturation using near-infrared spectroscopy by cerebral oximetry in pediatric cardiac surgery patients. Paediatr Anaesth 2005; 15:495-503.
88. U. Utzinger and R. R. Richards-Kortum, Fiber optic probes for biomedical optical spectroscopy, J Biomed Optics. 8(1) (2003), 121-147.
89. Van Beekvelt M C, Colier W N, Wevers R A, Van Engelen BGM. Performance of near-infrared spectroscopy in measuring local Oxygen consumption and blood flow in skeletal muscle. J Appl Physiol 2001; 90:511-519.
90. Van der Sluijs M C, Colier W N J M, Houston R J F, Oesburg B. A new and highly sensitive continuous wave near infrared spectrophotometer with multiple detectors. Proc SPIE. 1997; 3194:63-72.
91. Vasconcelos, M., E. Lima, et al. (2006). "Voiding dysfunction in children. Pelvic-floor exercises or biofeedback therapy: a randomized study." Pediatr Nephrol 21(12): 1858-64.
92. Vaux E C, Taylor D J, Altmann P, Rajagopalan B, Graham K, Cooper R, Bonomo Y, Styles P. Effects of carnitine supplementation on muscle metabolism by the use of magnetic resonance spectroscopy and near-infrared spectroscopy in end-stage renal disease. Nephron Clin Pract 2004; 97:c41-8.
93. Von Vierordt H. Die quantitative Spectralanalyse in ihrer Anwendung auf Physiologie, Physik, Chemie und Technologie. Tubingen H. Laupp, ed. 1876.
94. W. Cui, C. Kumar, and B. Chance, Experimental study of the migration depth for the photons measured at sample surface. Time resolved spectroscopy and imaging, Proc Int Soc Opt Eng. 1431 (1991), 180-91.
95. Ward K R, Ivatury R R, Barbee R W, Terner J, Pittman R. Torres Filho I P, Spiess B. Near infrared spectroscopy for evaluation of the trauma patient: a technology review. Resuscitation. 2006; 68:27-44

96. Watkin S L, Spencer S A, Dimmock P W, Wickramasinghe Y A, Rolfe P. A comparison of pulse oximetry and near infrared spectroscopy (NIRS) in the detection of hypoxaemia occurring with pauses in nasal airflow in neonates. J Clin Monit Comput 1999; 15:441-447.

97. Wolf M, Ferrari M. Progress of near-infrared spectroscopy and topography for brain and muscle clinical applications. J Biomed Optics 2007; 12(6):062104.

98. Wyatt J S, Cope M. Delpy D T, Wray S, Reynolds E O R. Quantification of cerebral oxygenation and haemodynamics in sick newborn infants by near infrared spectrophotometry. Lancet 1986; 2:1063-6.

99. Zaak D. Kriegmair M, Stepp H. Stepp H. Baumgartner R, Oberneder R, Schneede P. Corvin S, Frimberger D. Knüchel R. Hofstetter A. Endoscopic detection of transitional cell carcinomas with 5-aminolevulinic acid—results of 1012 fluorescent endoscopies. Urology 2001; 57:690-4.

The invention claimed is:

1. A device for use in non-invasive monitoring of con action of at least one selected muscle from within a vaginal lumen of a subject, comprising:

an elongate probe body configured for placement in the vaginal lumen, the probe body having a generally smooth external surface and is sized and shaped such that at least a portion of said external surface is configured for placement against a wall of the vaginal lumen apposing the at least one selected muscle, wherein said portion of the external surface defines at least one region of the probe body that is composed of a material that is generally transparent to near infrared (NIR) light to permit NIR light to pass through the probe body;

means for emitting NIR light housed within the probe body and positioned for emitting the NIR light through the at least one region of the probe body that is composed of said material, wherein the emitting means comprises a NIR light source or is connected by a light guide to an interface configured to be operably connected to an external NIR light source; and means for collecting NIR light housed within the probe body and positioned for receiving NIR light that enters the probe body through the at least one region of the probe body that is composed of said material and which is spaced apart from the means for emitting by a distance of about 1 to about 3 cm, wherein the collecting means comprises a NIR light detector or is connected by a light guide to an interface configured to be operably connected to an external NIR light detector.

2. The device of claim 1, wherein the distance is about 1, about 1.5 or about 2 cm.

3. The device of claim 1, wherein distance is about 2 cm.

4. The device of claim 1, wherein the means for emitting and collecting are located along a longitudinal side of the probe body.

5. The device of claim 4, further comprising a handle connected to the probe body that is configured to be outside the vaginal lumen when the device is in use and wherein the handle is at an angle to the probe body that is aligned with the means for emitting and collecting.

6. The device of claim 1, comprising two of said means for collecting, wherein the means for emitting is positioned between the two means for collecting.

7. The device of claim 6, wherein the means for collecting are independently spaced apart from the means for emitting by about 1, about 1.5 or about 2 cm.

8. The device of claim 6, wherein the means for emitting and collecting are located along a longitudinal side of the probe body and wherein the means for collecting are each spaced apart from the means for emitting by about 2 cm.

9. The device of claim 1, further comprising a handle connected to the probe body that is configured to be outside the vaginal lumen when the device is in use.

10. A near infrared (NIR) spectrophotometric system for non-invasive monitoring of contraction of at least one selected muscle from within a vaginal lumen of a subject, the system comprising:

an elongate probe body configured for placement in the vaginal lumen, the probe body having a generally smooth external surface and is sized and shaped such that at least a portion of said external surface is configured for placement against a wall of the vaginal lumen apposing the at least one selected muscle, wherein said portion of the external surface defines at least one region of the probe body that is composed of a material that is generally transparent to NIR light to permit NIR light to pass through the probe body;

means for emitting NIR light housed within the probe body and positioned for emitting the NIR light through the at least one region of the probe body that is composed of said material;

means for collecting NIR light housed within the probe body and positioned for receiving NIR light that enters the probe body through the at least one region of the probe body that is composed of said material and which is spaced apart from the means for emitting by a distance of about 1 to about 3 cm;

a source of NIR light in operative communication with the means for emitting; and means for detecting NIR light that is in operative communication with the means for collecting, to detect the NIR light when received by the means for collecting.

11. The system of claim 10, further comprising means for displaying the NIR light detected.

12. A non-invasive method for detecting a signal that is modulated by activity of a selected muscle in a subject, comprising:

placing an elongate probe into a vaginal lumen of the subject, the probe comprising a body having a generally smooth external surface a portion of which is placed against a wall of the vaginal lumen apposing the at least one selected muscle and wherein said portion of the external surface defines at least one region of the probe body that is composed of a material that is generally transparent to NIR light to permit NIR light to pass through the probe body; wherein the probe body further comprises means for emitting NIR light housed within the probe body and positioned for emitting the NIR light through the at least one region of the probe body that is composed of said material, the means for emitting comprising or being in operative communication with a NIR light source and means for collecting NIR light housed within the probe body and positioned for receiving NIR light that enters the probe body through the at least one region of the probe body that is composed of said material, the collector comprising or being in operative communication with a NIR light detector, the means for collecting being spaced apart from the means for emitting by a distance of about 1 to about 3 cm;

causing a NIR light signal to be emitted from the means for emitting, which light signal travels to the selected muscle by traversing said all of the vaginal lumen;

receiving the NIR light signal when it returns to the probe body by said means for collecting; and detecting the received NIR light signal with the detector.

13. The method of claim 12, further comprising monitoring the detected NIR light signal over time.

14. The method of claim 12, further comprising displaying the detected NIR light signal over time.

15. The method of claim 12, further comprising displaying a change in the detected NIR light signal.

16. The method of claim 12, further comprising deriving a rate of change in oxyhemoglobin from a change in the detected NIR light signal over time.

17. The method of claim 12, wherein the selected muscle is a urethral sphincter or a detrusor muscle of the subject's posterior bladder wall.

18. The method of claim 12, wherein the subject makes voluntary muscle contractions in a region of the subject where the selected muscle is located, while the NIR light signal is emitted.

19. The method of claim 18, wherein the voluntary muscle contractions comprise contractions of one or more pelvic floor muscles.

20. The method of claim 18, wherein the subject changes the voluntary muscle contractions that are made to cause a change in the detected NIR light signal.

21. The method of claim 12, wherein the probe body is connected to a handle and the method further comprises using the handle to position and stabilize the probe body against the wall of the vaginal lumen.

\* \* \* \* \*